United States Patent
Wöhrle et al.

(10) Patent No.: US 7,163,908 B2
(45) Date of Patent: Jan. 16, 2007

(54) METATHESIS CATALYSTS

(75) Inventors: Ingo Wöhrle, Holzminden (DE); Peter Esser, Summerville, SC (US); Aurélia Reckziegel, Holzminden (DE); Matthias Brandt, Düsseldorf (DE); Stephen Klein, Bergisch Gladbach (DE); Thomas Turek, Düsseldorf (DE)

(73) Assignee: Symrise GmbH & Co. KG, Holzminden (DE)

( * ) Notice: Subject to any disclaimer, the term of this patent is extended or adjusted under 35 U.S.C. 154(b) by 0 days.

(21) Appl. No.: 11/104,800

(22) Filed: Apr. 13, 2005

(65) Prior Publication Data

US 2005/0202961 A1     Sep. 15, 2005

Related U.S. Application Data

(62) Division of application No. 10/227,137, filed on Aug. 23, 2002, now Pat. No. 6,903,241.

(30) Foreign Application Priority Data

Aug. 28, 2001 (DE) ................. 101 42 033

(51) Int. Cl.
  *B01J 27/14* (2006.01)
  *B01J 23/04* (2006.01)
  *B01J 23/36* (2006.01)

(52) U.S. Cl. ............... 502/208; 502/344; 502/349; 502/352; 502/355

(58) Field of Classification Search ............... 502/208, 502/344, 349, 352, 355
See application file for complete search history.

(56) References Cited

U.S. PATENT DOCUMENTS

| | | | | |
|---|---|---|---|---|
| 3,594,440 A | * | 7/1971 | McGrath | 585/647 |
| 3,637,892 A | * | 1/1972 | McGrath | 585/645 |
| 3,707,581 A | * | 12/1972 | Heckelsberg | 585/643 |
| 4,409,148 A | * | 10/1983 | Qualeatti et al. | 554/142 |
| 4,824,869 A | * | 4/1989 | Prada-Silva et al. | 518/714 |
| 4,880,763 A | * | 11/1989 | Eri et al. | 502/302 |
| 4,885,410 A | * | 12/1989 | De Thomas | 568/861 |
| 5,449,852 A | * | 9/1995 | Chauvin et al. | 585/647 |
| 6,908,878 B1 | * | 6/2005 | Euzen et al. | 502/241 |
| 2003/0008766 A1 | * | 1/2003 | Kruger-Tissot et al. | 502/24 |

FOREIGN PATENT DOCUMENTS

GB       1552368      9/1979

* cited by examiner

*Primary Examiner*—Elizabeth D. Wood
(74) *Attorney, Agent, or Firm*—Stephan Pendorf; Akerman & Senterfitt

(57) ABSTRACT

The present invention relates to supported catalysts based on $Re_2O_7/(-Al_2O_3)$ for use in the preparation of cycloalkadienes in a metathesis reaction, a process for preparing cycloalkadienes in the presence of these supported catalysts and also the use of the resulting cycloalkadienes for preparing fragrances.

5 Claims, 1 Drawing Sheet

METATHESIS CATALYSTS

CROSS REFERENCE TO RELATED APPLICATIONS

This application is a Divisional Application of U.S. application Ser. No. 10/227,137 filed on Aug. 23, 2002, which issued as U.S. Pat. No. 6,903,241 on Jun. 7, 2005, and which is hereby incorporated in their entirety by reference.

FIELD OF THE INVENTION

The present invention relates to supported catalysts based on $Re_2O_7/\gamma$-$Al_2O_3$ for use in the preparation of cycloalkadienes in a metathesis reaction, a process for preparing cycloalkadienes in the presence of these supported catalysts, and also the use of the cycloalkadienes prepared.

BACKGROUND OF THE INVENTION

Cycloalkenes, preferably cycloalkadienes having a ring size of from 12 to 18 carbon atoms, are used, inter alia, for preparing oxygen-containing, macrocyclic compounds. The compounds can be used in the preparation of macrocyclic ketones, lactones and epoxides, which are prized as musk fragrances in the perfume industry.

EP-A 182 333 discloses the catalyst system $Re_2O_7/\gamma$-$Al_2O_3/SnR_4$, where R is an alkyl radical, which can be used for converting highly diluted cycloolefin solutions in the liquid phase into the corresponding cycloalkadienes by a metathesis reaction.

The preparation of cycloalkadienes in the liquid phase in the presence of a supported catalyst based on $Re_2O_7/\gamma$-$Al_2O_3$ by a metathesis reaction of cyclooctenylenes having a degree of polymerization greater than, or equal to three, and/or cycloalkamonoenes is described in EP-A 343 437.

The metathesis of methyl oleate using the catalyst system $Re_2O_7/\gamma$-$Al_2O_3/SnR_4$ is described in Applied Catalysis 1991, 67, 279. The pore volume of this pulverulent catalyst was 0.48 g/cm$^3$ at an $Re_2O_7$ content of 3.1%.

The metathesis of unsaturated esters over $Re_2O_7/\gamma$-$Al_2O_3$ catalysts is known from Journal of Molecular Catalysis 1985, 28, 141. The pore volume of this pulverulent catalyst was 0.36 g/cm$^3$ at an $Re_2O_7$ content of 5.0%.

Metathesis catalysts based on $Re_2O_7/\gamma$-$Al_2O_3$ are described in Catalysis Letters 1991, 8, 201. A 180–250 µm aluminum oxide particle fraction was doped with 2.2% by weight of phosphorus by digestion. The pore volume of this pulverulent support material was 0.38 g/cm$^3$ without a Re component.

Due to the necessarily high dilution of the cycloolefin solutions used in the metathesis reaction, the amount of cycloalkadienes obtainable per unit time has been unsatisfactory from economic, engineering and industrial points of view.

SUMMARY OF THE INVENTION

It is an object of the invention to provide supported catalysts and processes by means of which a larger amount of cycloalkadienes can be obtained per unit time. It is greatly advantageous to achieve a higher productivity and a higher space-time yield in the metathesis process.

DETAILED DESCRIPTION OF THE INVENTION

Figure 1:
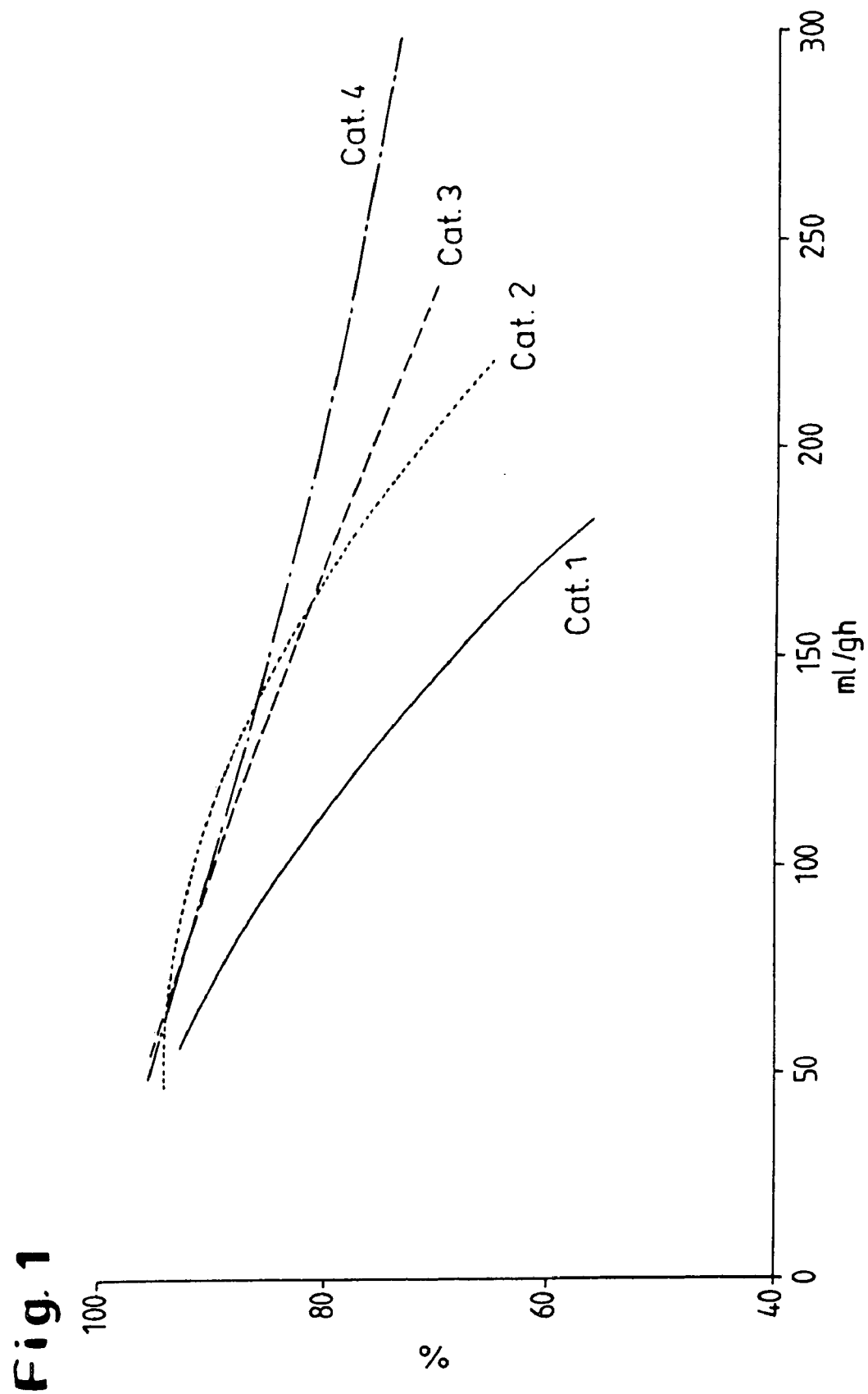
FIG. 1 shows, in graph form, the cyclooctene-based conversion as a function of the space velocity in a metathesis reaction using the supported catalysts of the invention in comparison with a commercially available swirl-strand supported catalyst Cat. 1.

Surprisingly, it has been found that supported catalysts having a high pore volume can achieve a significant increase in the activity and productivity of the supported $Re_2O_7/\gamma$-$Al_2O_3$ catalyst. This is particularly noticeable at relatively high space velocities, as a result of which the amount of cycloalkadienes obtainable per unit time can be significantly increased. Furthermore, it has surprisingly been found that the supported catalysts of the present invention have a greater operating life, as a result of which, more metathesis products and cycloalkadienes can be prepared within a supported catalyst cycle. In addition, the supported catalysts have a higher total life.

Accordingly, the invention provides a process for preparing cycloalkadienes from cycloalkamonoenes, cyclopolyenes, acyclic polyenes or mixtures thereof in the liquid phase by a metathesis reaction in the presence of a supported catalyst based on $Re_2O_7/\gamma$-$Al_2O_3$, characterized in that the pore volume of the supported catalyst is greater than, or equal, to 0.6 cm$^3$/g.

The present invention further provides supported catalysts for a metathesis reaction, which have a pore volume of greater than, or equal to, 0.6 cm$^3$/g and contain $\gamma$-$Al_2O_3$ as support material, from 1 to 12% by weight of $Re_2O_7$, from 0 to 30% by weight of tin and from 0.2 to 3% by weight of cesium and/or from 0.3 to 3% by weight of phosphorus, with the $\gamma$-$Al_2O_3$ support material being able, if desired, to be treated with an acid before application of the rhenium. The present invention also provides for the use of these supported catalysts in a metathesis reaction.

The cycloalkadienes which are obtainable by the process of the present invention can be used for the preparation of fragrances, in particular for the preparation of macrocyclic fragrances.

For the purposes of the present invention, the metathesis solution is the starting solution, i.e. a solvent containing at least one hydrocarbon selected from the group of cycloalkamonoenes, cyclopolyenes, or acyclic polyenes.

FIG. 1 shows, in graph form, the cyclooctene-based conversion (in percent, x axis) as a function of the space velocity (in ml/gh, y axis) in a metathesis reaction using the supported catalysts of the invention (Cat. 2 to 4, pore volume>0.6 cm$^3$/g) in comparison with a commercially available swirl-strand supported catalyst Cat. 1 (pore volume: 0.45 cm$^3$/g). The supported catalysts of the present invention display a significantly higher activity, as a result of which a higher space-time yield and a higher productivity of cycloalkadienes can be achieved. The supported catalysts are described in more detail in Table 1 and in Example 1, and the experimental conditions are described in more detail in Example 2.

The supported catalysts of the invention have a pore volume of greater than, or equal to, 0.6 cm$^3$/g, preferably from 0.7 to 1.3 cm$^3$/g.

The determination of the pore volumes was carried out by means of mercury porosimetry over a pressure range from 0.01 mbar to 4000 bar. This enabled a pore range from 38 Å to 14 μm to be measured.

The supported catalysts of the invention typically have specific surface areas of from 100 to 300 m²/g determined by the BET method (Brunauer, Emmett and Teller method).

The supported catalysts are preferably used as shaped bodies such as hollow rods, extrudates, ram extrudates, spheres, cylinders, cubes, cones and the like. Preference is given to spheres, swirl strands (SS) or cylinders.

Preference is given to a continuous reaction procedure, more preferably, a vertical arrangement of the supported catalysts in a fixed bed, in which case the metathesis solution advantageously flows through the fixed bed from the bottom upwards.

The Re$_2$O$_7$ content of the supported catalyst, based on the weight of the supported catalyst, is advantageous in the range from 1 to 12% by weight, preferably in the range from 2 to 8% by weight, more preferably, in the range from 3 to 6% by weight. The supported catalysts are produced by methods known to those skilled in the art. The rhenium is usually applied by impregnation of the support material with an aqueous solution of one or more rhenium compounds and subsequent thermal treatment of the material, resulting in formation of Re$_2$O$_7$ Suitable rhenium compounds are, for example, perrhenates such as ammonium perrhenate; it is also possible to use perrhenic acid or Re.sub.2O.sub.7 itself. The thermal treatment of the supported catalyst is carried out in a temperature range from 200 to 600° C., with the maximum usable temperature being in the region of about 600° C.

It is preferably advantageous for the supported catalyst to contain from 0.5 to 40% by weight, more preferably, from 1 to 20% by weight, and most preferably, from 1 to 10% by weight, of a tin tetraalkyl or tin dioxide or a mixture of these tin compounds.

Preferred tin tetraalkyls are tetramethyltin, tetraethyltin, tetra-n-butyltin, tetra-n-octyltin; more preference is given to tetramethyltin. It is most preferred for the supported catalyst to be brought into contact with a solution containing a tin tetraalkyl before commencement of the metathesis reaction. In this case, it is also possible to use mixtures of the tin tetraalkyls mentioned. Application of tin dioxide can be carried out, for example, in the regeneration of the supported catalyst containing a tin tetraalkyl, but can also be achieved by impregnating the supported catalyst with water-soluble tin compounds and subsequently heating it at 500–600° C. in an oxygen-containing atmosphere, resulting in the formation of tin oxide.

Furthermore, it is advantageous for the metathesis reaction to be carried out in the presence of a tin tetraalkyl. The tin tetraalkyls are typically added to the metathesis solution before commencement of the metathesis reaction, and this mixture is conveyed from a reservoir over the bed of supported catalyst. The tin tetraalkyls are typically added to the metathesis solution in an amount of from 0.1 to 8% by weight, preferably from 0.1 to 5% by weight, more preferably, from 0.1 to 2.5% by weight, based on the weight of the supported catalyst. Preferred tin tetraalkyls are tetramethyltin, tetraethyltin, tetra-n-butyltin, tetra-n-octyltin; more preferably, tetramethyltin.

The content of cycloalkamonoenes, cyclopolyenes, acyclic polyenes or mixtures thereof in the liquid phase is typically in the range from 0.5 to 10 g/l, preferably in the range from 1.0 to 5.5 g/l, most preferably, in the range from 2.0 to 4.0 g/l.

The starting materials are used in metathesis-inert solvents. Suitable solvents are, for example, hydrocarbons and halogenated hydrocarbons, in particular butane, pentane, hexane, heptane, octane, cyclopentane, cyclohexane, cyclooctane, dichloromethane and trichloroethane. Preference is given to n-pentane, n-hexane, n-heptane, n-octane, isooctane, cyclopentane and cyclohexane, more preferably, n-pentane and n-hexane. It is also possible to use mixtures of hydrocarbons, e.g. petroleum ether.

Advantageous cycloalkamonoenes are those having a ring size of from 4 to 12 carbon atoms. Preferred cycloalkamonoenes are cyclopentene, cyclohexene, cycloheptene, cyclooctene, cyclononene, cyclodecene and cyclododecene. More preferably, cycloheptene and cyclooctene.

Preferable cyclopolyenes or acyclic polyenes are those which can be obtained from the cycloalkamonoenes mentioned. The cyclopolyenes or acyclic polyenes can be formed, for example, as by-products in metathetic dimerizations, by ring-opening metatheses or polymerizations. In general, the cyclopolyenes and the acyclic polyenes have a degree of polymerization of from 3 to 50, preferably from 3 to 20. For the purposes of the present invention, the degree of polymerization is the number of monomer units, identical or different, of which the polyene is built up.

According to the present invention, preferred cyclopolyenes are polymers or copolymers of the cycloalkamonoenes mentioned, with the cyclopolyenes having a degree of polymerization of greater than or equal to three, preferably from 3 to 50, more preferably from 3 to 20. Preference is given to using cyclopolyenes of cycloheptene, cyclooctene or their copolymers.

Most preferably, cyclopolyenes are cyclopolyoctenylenes of the formula 1

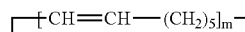

having a degree of polymerization m of at least 3, where m is preferably in the range from 3 to 50, more preferably in the range from 3 to 20.

Cycloalkamonoenes, cyclopolyenes, acyclic polyenes can be present in the metathesis solutions in any compositions and mixing ratios.

Preference is given to metathesis solutions containing cycloalkamonoenes. If metathesis solutions containing only cycloalkamonoenes as olefinic compounds are used, preference is given to cycloheptene, cyclooctene or mixtures thereof. Preference is also given to mixtures of cycloalkamonoenes and cyclopolyenes, with mixtures containing cycloheptene, cyclooctene or a mixture thereof and cyclopolyheptenylene, cyclopolyoctenylene, copolymers of cycloheptene and cyclooctene or a mixture thereof being more preferred.

If mixtures of cycloalkamonoenes and cyclopolyenes are used, the preferred mixing ratio is in the range 0.1–2:1, more preferably 0.2–1:1.

More preference is given to a mixture of cyclooctene and cyclopolyoctenylene, in which case preference is given to a ratio of cyclooctene to cyclopolyoctenylenes in the range 0.25–0.5:1.

If cycloalkamonoenes or mixtures containing cycloalkamonoenes are used in the metathesis reaction, it is advantageous to set a conversion, based on the content of cycloalkamonoenes, in the range from 40 to 99%, preferably in the range from 50 to 95%, most preferably in the range from 60 to 85%.

The metathesis solution can also contain small proportions of cycloalkadienes, preferably the cycloalkadienes to be formed, i.e. product cycloalkadienes. These can be present in small amounts in the cycloalkamonoenes, cyclopolyenes or the acyclic polyenes and may result, for example, from distillation.

Preferred cycloalkadienes which can be prepared by the process of the present invention have from 12 to 18 carbon atoms. More preferred cycloalkadienes are 1,8-cyclotetradecadiene, 1,8-cyclopentadecadiene and 1,9-cyclohexadecadiene. Most preferred is given to 1,9-cyclohexadecadiene.

It is advantageous to treat the supported catalyst with one or more mineral acids, which can be carried out before or after application of the rhenium. Preference is given to treating the γ-$Al_2O_3$ support material or the Re-laden supported catalyst with an aqueous HCl solution.

Also advantageous are supported catalysts containing from 0.2 to 3% by weight of cesium, with the treatment with one or more cesium compounds being able to be carried out before or after the application of the rhenium. Preference is given to treatment with an aqueous cesium nitrate solution.

Also advantageous are supported catalysts containing from 0.3 to 3% by weight of phosphorus, with the treatment with one or more phosphorus compounds being able to be carried out before or after the application of the rhenium. Preference is given to treatment with an aqueous ammonium phosphate solution, most preferably a solution of diammonium hydrogen phosphate.

Further preferred supported catalysts for a metathesis reaction having a pore volume of greater than or equal to 0.6 cm.sup.3/g comprise γ-$Al_2O_3$ as support material, from 1 to 12% by weight of $Re_2O_7$, from 0 to 30% by weight of tin and also from 0.2 to 3% by weight of cesium and/or from 0.3 to 3% by weight of phosphorus.

The above-mentioned dopants, active constituents or treatments are preferably applied to the supported catalyst by impregnation, but production of the supported catalysts by means of digestion is also possible.

The metathesis reaction can be carried out at temperatures in the range from 0 to 100° C.; preference is given to a temperature in the range from 25 to 80° C., most preferably one in the range from 35 to 60° C.

When using solvents having boiling points below the reaction temperature, the reaction can be carried out under superatmospheric pressure. In general, the metathesis reaction can be carried out at a pressure in the range from 1 to 10 bar abs.

After use in the metathesis reaction, the supported catalyst can be regenerated and reused in the metathesis reaction. The supported catalyst can, as described, for example, in EP-B1-991 467, be removed from the metathesis reactor, washed with a metathesis-inert solvent and subsequently dried. Thermal treatment of the supported catalyst in the regeneration is carried out in a temperature range from 200 to 600.degree. C., with the maximum usable temperature being about 600° C. Thermal treatment is carried out in an oxygen-containing atmosphere, for example air which can, if desired, be admixed with inert gases such as nitrogen or argon.

EXAMPLES

The invention is further illustrated, but is not intended to be limited by the following examples in which all parts and percentages are by weight unless otherwise specified.

Example 1

The support materials containing γ-$Al_2O_3$ were procured commercially (e.g. from Condea, or KataLeuna). The pore volumes were typically from 0.6 to 1.2 $cm^3/g$. Application of $Re_2O_7$, and, possibly further compounds, according to the present invention, to the support materials resulted in the pore volumes being essentially maintained.

Ammonium perrhenate is dissolved in a dioxane/water mixture (80/20 v/v), and the γ-$Al_2O_3$ is added thereto in the form of shaped bodies. The mixture was impregnated at the boiling point for 12 hours, the supernatant solution was decanted off, and the catalyst was dried at 120° C. After treatment for two hours at 500–580° C. in a stream of air, the catalyst was maintained at the same temperature for 2 hours in a stream of nitrogen and subsequently cooled to room temperature. The physical characterization is shown in Table 1.

TABLE 1

| $Re_2O_7$-containing supported catalysts | | | | | |
|---|---|---|---|---|---|
| | | Cat 1 | Cat 2 | Cat 3 | Cat 4 |
| | | Shape | | | |
| | | SS | SS | SS | Sphere |
| Diameter ∅ | mm | 1.4 | 1.3 | 1.2 | 1.5–2.5 |
| Density | kg/l | 0.55 | 0.58 | 0.54 | 0.43 |
| Pore volume | $cm^3/g$ | 0.45 | 0.7 | 0.8 | 1.2 |
| BET surface area | $m^2/g$ | 218 | 246 | 120 | 231 |
| $Re_2O_7$ | % by weight | 3.6 | 3.5 | 3.5 | 3.6 |
| γ-$Al_2O_3$ | % by weight | 96.0 | 95.8 | 96.0 | 95.9 |

Cat 1 is a commercially available catalyst and was procured from KataLeuna.

The length of the swirl strands (SS) was typically in the range from 10 to 19 mm.

The supported catalysts Cat 2, Cat 3, and Cat 4 listed in Table 1 were produced by the method described in Example 1.

Example 2

50 g of one of the supported catalysts shown in Table 1 were in each case placed in a vertical tube reactor (height: 50 m, diameter: 1.5 cm) under a protective gas atmosphere (argon). A solution of 2.5% by weight of tetramethyltin (based on the weight of the supported catalyst); the n-hexane was circulated by means of a pump through the fixed bed of supported catalyst from the bottom upwards at 25.degree. C. for 3 hours. A solution containing 2.4 g of cyclooctene and 0.5% by weight of tetramethyltin (based on the weight of the supported catalyst) per liter of n-hexane was then passed continuously from the bottom upwards through the bed of the supported catalyst at 45° C. and atmospheric pressure.

The amount of metathesis solution passed over the bed of supported catalyst per unit time, i.e. the space velocity, was varied by means of the pump output.

The selectivity to 1,9-cyclohexadecadiene was 36–38% over the entire reaction. The selectivity to 1,9-cyclohexadecadiene and cyclopolyoctenylenes was 99%.

The conversions achieved are shown as a function of the space velocity in FIG. 1. FIG. 1 shows, in graph form, the cyclooctene-based conversion (in percent, x axis) as a function of the space velocity (in ml/gh, y axis) in a metathesis reaction using the supported catalysts of the invention (Cat. 2 to 4) in comparison with supported catalyst Cat. 1 (pore volume: 0.45 cm$^3$/g). The supported catalysts of the present invention display a significantly higher activity.

Example 3

γ-Al$_2$O$_3$ (242 g) in the form of 2.5 mm spheres (obtainable from Condea, pore volume: 0.81 cm$^3$/g) was impregnated with a solution of rhenium oxide (9 g in 120 g of water) and subsequently dried. After treatment at 500–580° C. in a stream of air for 2 hours, the catalyst was kept at the same temperature in a stream of nitrogen for a further 2 hours and subsequently cooled to room temperature. After impregnation with 125 ml of an aqueous solution of 1.8 g of cesium nitrate, the catalyst was dried at 120° C. for two hours, followed by treatment at 500° C. in a stream of air for two hours and cooling in a stream of nitrogen. This gave a supported catalyst having a pore volume of 0.79 cm$^3$/g and containing 3.7% by weight of Re$_2$O$_7$ and 0.5% by weight of cesium.

Example 4

γ-Al$_2$O$_3$ (250 g) in the form of swirl strands (procured from KataLeuna) was impregnated with a solution of diammonium hydrogen phosphate (25 g of 1 l of distilled water) at 80° C. for 6 hours, filtered, washed with 1 l of distilled water, dried and calcined at 580° C. for 18 hours. This material was subsequently impregnated with an aqueous solution of ammonium perrhenate (17 g in 130 ml of distilled water) and dried. After treatment at 500–580° C. in a stream of air for two hours, the catalyst was kept at the same temperature in a stream of nitrogen for a further 2 hours and subsequently cooled to room temperature. This gave a supported catalyst having a pore volume of 0.74 cm$^3$/g and containing 3.6% by weight of Re$_2$O$_7$ and 1.1% by weight of phosphorus.

Example 5

.gamma.-Aluminum oxide (240 g) in the form of swirl strands (obtainable from Condea, pore volume: 0.66 cm$^3$/g) was impregnated with an aqueous solution of ammonium perrhenate (16.5 g in 240 ml of distilled water) and dried. After further impregnation with 120 ml of an aqueous solution of 2.25 g of hydrogen chloride, the catalyst was dried, treated at 500–580° C. in a stream of air for 2 hours and at the same temperature in a stream of nitrogen for a further 2 hours. After cooling to room temperature, a supported catalyst having a pore volume of 0.65 cm$^3$/g and containing 3.6% by weight of Re$_2$O$_7$ was obtained.

Although the invention has been described in detail in the foregoing for the purpose of illustration, it is to be understood that such detail is solely for that purpose, and that variations can be made therein by those skilled in the art without departing from the spirit and scope of the invention except as it may be limited by the claims.

What is claimed is:

1. A supported catalyst for a metathesis reaction comprising:
    a) gamma-Al$_2$O$_3$ as support material,
    b) 1 to 12% by weight of Re$_2$O$_7$,
    c) 0 to 30% by weight of tin,
    and also at least one of the following constituents:
    d) from 0.2 to 3% weight of cesium,
    e) from 0.3 to 3% by weight of phosphorus,
    wherein the supported catalyst has a pore volume greater than or equal to 0.6 cm$^3$/g, and wherein the catalyst is free of a catalytically active amount of niobium and/or tantalum.

2. The supported catalyst according to claim 1, wherein the pore volume of the supported catalyst is in the range from 0.7 to 1.3 cm$^3$/g.

3. The supported catalyst according to claim 1, wherein the supported catalyst has a surface area from 100 to 300 m$^2$/g.

4. The supported catalyst according to claim 1, wherein the supported catalyst forms a shaped body.

5. The supported catalyst according to claim 4, where the shaped body is chosen from hollow rods, extrudates, ram extrudates, spheres, cylinders, cubes, and cones.

* * * * *